United States Patent [19]

Schirmer

[11] Patent Number: 5,912,722
[45] Date of Patent: Jun. 15, 1999

[54] SCALE CORRECT OPTHAMALIC MICROSCOPE USING SLIT BEAM ILLUMINATION

[76] Inventor: Kurt E. Schirmer, 56 Granville Road, Hampstead, Quebec, Canada, H3X 3B6

[21] Appl. No.: 08/855,715

[22] Filed: May 8, 1997

Related U.S. Application Data

[60] Provisional application No. 60/028,146, May 9, 1996.

[51] Int. Cl.⁶ ........................................................ A61B 3/10
[52] U.S. Cl. ............................................ 351/221; 351/205
[58] Field of Search ..................................... 351/214, 221, 351/211, 205, 206, 200, 246, 247

[56] References Cited

U.S. PATENT DOCUMENTS 4,669,837   6/1987   Schirmer ................................. 351/221

*Primary Examiner*—Hung Xuan Dang
*Attorney, Agent, or Firm*—Michael D. Bednarek; Crowell & Moring LLP

[57] ABSTRACT

The ophthalmic microscope has a slit beam light source mounted in a fixed relation to a telescopic objective lens for producing a slit beam which passes through a focal point of the objective lens in an image space before passing through the objective lens. The slit beam is thus fixed with respect to the objective lens to travel parallel to the optical axis of the objective lens in object space. The working distance can be varied without adjusting the illumination.

12 Claims, 2 Drawing Sheets

# SCALE CORRECT OPTHAMALIC MICROSCOPE USING SLIT BEAM ILLUMINATION

This application claims benefit of provisional application No. 60/028,146 filed May 9, 1996.

FIELD OF THE INVENTION

The present invention relates to an ophthalmic microscope of the type which is used for viewing or imaging the vitreous and retina of the eye. Such a microscope may also be used for directing laser beams into the eye for conducting ophthalmic surgery.

BACKGROUND OF THE INVENTION

Ophthalmic microscopes are well known in the art. An ophthalmoscope which includes a laser photocoagulator is disclosed in U.S. Pat. No. 4,669,873 granted to the present Applicant. Such ophthalmoscopes or ophthalmic microscopes are used to image the vitreous and retina of the eye, typically without the use of a contact lens. Illumination of the retina and vitreous is somewhat difficult due to the constraints of the relatively small sized pupil through which the vitreous and retina are viewed and also due to the fact that the vitreous does not allow light to pass freely through it without some scatter and absorption.

In U.S. Pat. No. 4,307,944 also granted to the present Applicant, a dual slit-lamp illumination system is disclosed which allows the fundus of the eye to be illuminated using the two slit beams.

It has been found that the prior art devices and the known methods of using the prior art devices do not yield scale correct image projection and do not provide good illumination which is easy to work with.

SUMMARY OF THE INVENTION

It is a first object of the present invention to provide a scale correct image projection of the vitreous and retina of the eye. It is a further object of the present invention to provide slit beam illumination that permits the required working distance between the eye and the objective lens of the ophthalmic microscope to be freely varied without adversely affecting illumination.

According to the invention, there is provided a method of obtaining a scale-correct desired microscope image of a vitreous and a retina of an eye comprising the steps of: providing a telescopic objective lens through which the vitreous and the retina of the eye can be imaged, the objective lens having an optical axis positioned to pass through a pupil of the eye; projecting a slit beam in a fixed relation to the objective lens such that the slit beam passes through a focal point of the lens in an image space of the lens before passing through the lens, and the slit beam travels parallel to the optical axis of the lens in an object space of the lens between the lens and the eye where the slit beam enters the pupil; and adjusting a distance between the lens and the eye to obtain the desired microscope image. Preferably, the desired microscope image is one in which a border of the pupil is in the periphery of the field of view.

The invention also provides an ophthalmic microscope comprising: a telescopic objective lens having an optical axis; a slit beam light source mounted in a fixed relation to the objective lens for producing a slit beam which passes through a focal point of the objective lens in an image space before passing through the objective lens, the slit beam traveling parallel to the optical axis in an object space of the objective lens; and field lens means for providing a spatially-correct microscope image through the objective lens of a vitreous and a retina of the eye.

Preferably, the telescopic objective lens has an optical power of approximately 45 diopters which is three quarters of the power of the lens of the human eye such that the ratio between the power of the telescopic objective lens and the power of the human eye lens respects the ratio between the refractive index of air and the refractive index of the vitreous of the eye. As can be appreciated, the apparatus according to the invention can be used with a camera to provide recorded images and a laser device can also be coupled into the optics as is known in the prior art so that the device can be used for laser surgery.

In a preferred form of the invention, the microscope can be described as being "symmetrically telecentric".

BRIEF DESCRIPTION OF THE DRAWINGS

The invention will be better understood by way of the following detailed description of a preferred embodiment with reference to the appended drawings in which.

DETAILED DESCRIPTION OF THE PREFERRED EMBODIMENT

Figure 1:
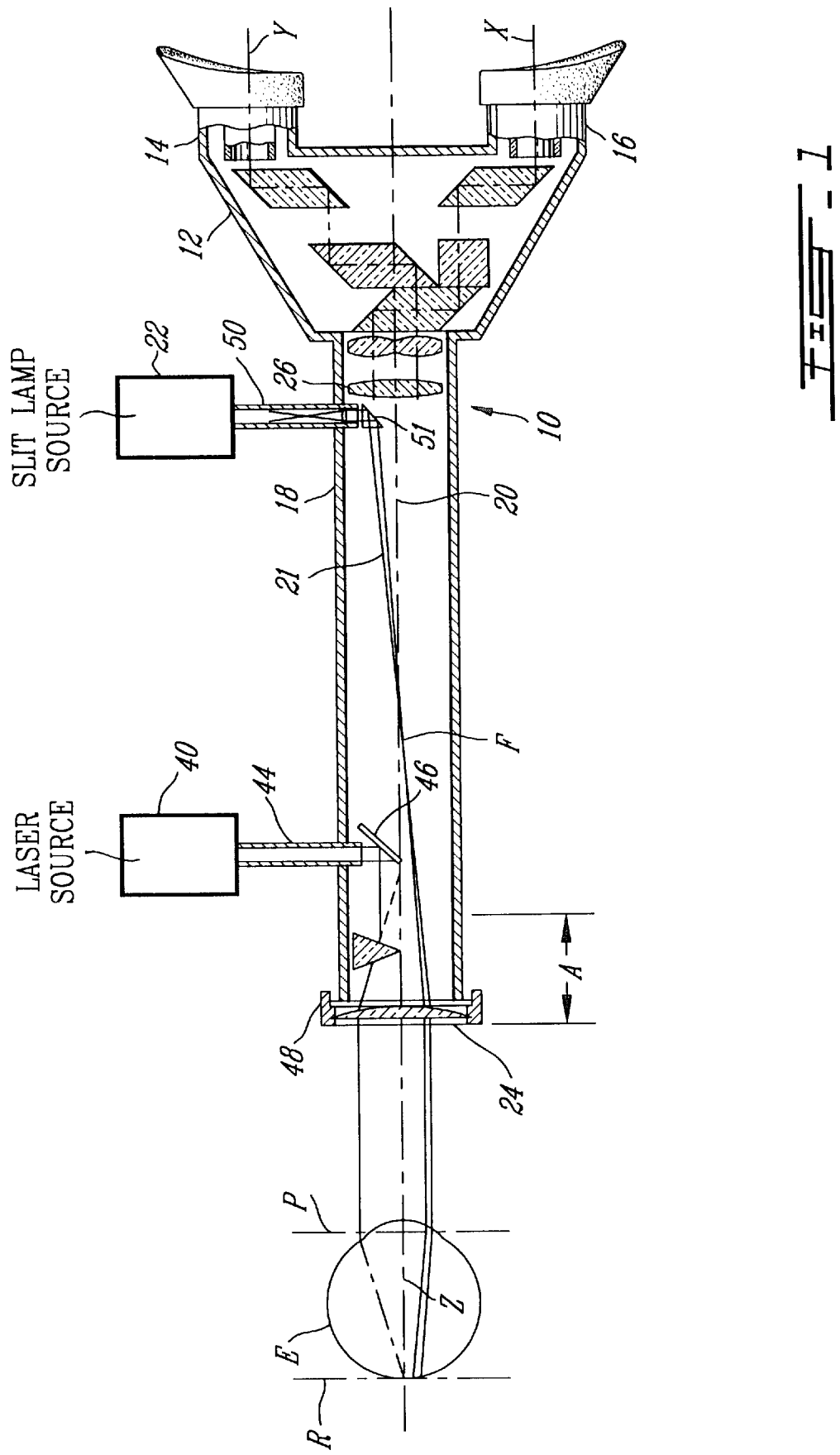
FIG. 1 illustrates a break-away plan view of the microscope according to the preferred embodiment, showing the binocular eyepiece turned 90° to better illustrate the eyepiece optics.

Illustrated in FIG. 1 is the ophthalmic microscope device 10 having an optical axis 20 positioned through the middle axis line Z of eye E. A slit lamp source 22 produces a slit lamp beam 21 which is directed to pass through the focal point f of the telescopic objective lens 24 such that the slit lamp beam 21 passes substantially parallel to the optical axis 20 from the objective 24 into the eye through the pupil at plane P. The slit lamp beam enters through the pupil, passes through the vitreous towards the retina at plane R. In so doing, the slit lamp beam 21 illuminates the vitreous and retina sufficiently for imaging. The width of the slit lamp beam 21 extends into the page in the diagram shown in FIG. 1. The image to be viewed through objective lens 24 is relayed to an eyepiece 12 through field lens 26. The binocular eyepiece 12 is shown in the diagram of FIG. 1 turned 90° for clarity of illustration such that the illumination beam is horizontal in the image viewed. The binocular eyepiece 12 includes oculars 14 and 16 through which the image can be viewed.

As can be seen, the beam 21 passes below the axis 20 in the object space. This could alternatively be provided to pass above the axis 20. The distance between the axis 20 and the beam 21 is fixed in the preferred embodiment to be suitable for good illumination of the fundus for an average size pupil under examination. Of course, it would be possible to provide an adjustment to the prism 51 to change the path of the beam 21 to pass through point f and strike lens 24 either closer or farther from axis 20. Alternatively, a second slit beam source could be provided to allow the user to choose between two beams at different distances from axis 20.

Figure 2:
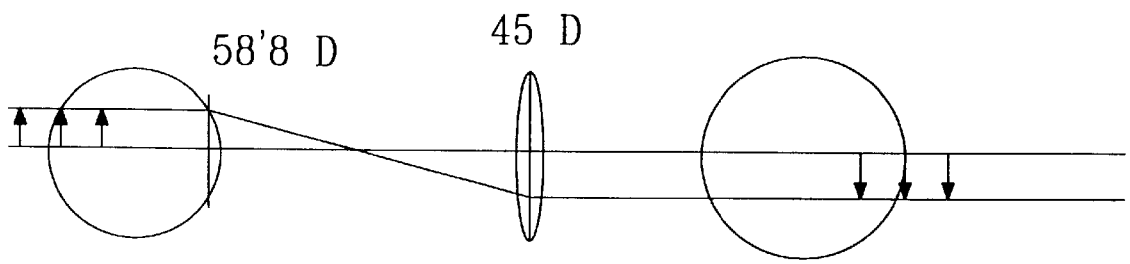
FIG. 2 is a schematic optical diagram illustrating spatially and scale-correct imaging of the vitreous.

In accordance with the invention, the slit lamp source 22 provides light in tube 50 through a slit and lens system as is known in the art through a prism 51 to direct the beam 21 through the focal point F. The slit lamp source 22 is mounted to the tube 18 of the housing of device 10 in such a way that the directing of the beam 21 through the focal point towards the objective lens 24 to exit parallel to the optic axis 20 and continue through the pupil into the vitreous of the eye. Image focus is achieved by adjusting the field lens 26 and eyepiece 12 with respect to the objective lens 24. The focus adjustment takes place without interfering with the fixed relationship between the slit lamp source and the objective lens 24. As illustrated in FIG. 2, the objective lens 24 preferably has a power of approximately 45 diopters so that the image viewed through lens 24 and through the lens of the eye which has approximately a strength of 58.8 diopters produces scale-correct imaging as a result of the relationship between these strengths being the same as the relationship between the index of refraction in air to water.

The laser source 40 and the laser light guiding tube 44 and relay optics consisting of mirror 46 and lens 48 may be provided to provide a source of laser light for laser surgery, although the provision of a laser source is considered optional in the preferred embodiment.

As can be appreciated, the distance between the objective lens 24 and the eye is greater in practice than is shown to scale in FIG. 1. The working distance between the eye and the objective lens 24 is greater than what would be present in the prior art Gullstrand fundus microscope method. As can be further appreciated, since the illumination beam 21 travels parallel to the optical axis between the lens 24 and the eye, the distance between the eye and the lens will not adversely affect illumination.

Figure 3:
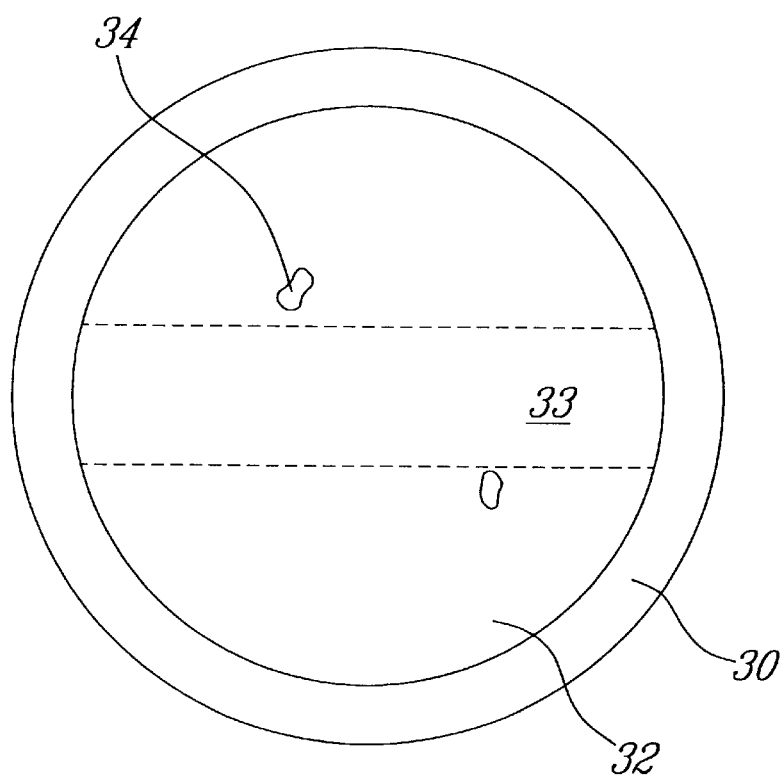
FIG. 3 illustrates a field of view in the preferred embodiment in which the periphery of the pupil is at an image periphery.

As shown in FIG. 3, the field of view is adjusted to leave a small border 30 outside the pupil 32 in the periphery of the image. The slit beam 21 provides a brighter area 33 on the retina, and floaters 34 in the vitreous appear scale correct. The spatially-correct image results from the symmetrical telecentric optics. With the power of the objective lens selected to be 45 diopters (see FIG. 2), the objects in the vitreous appear dimensionally correct, that is, their height, width and depth are in the same proportions in the image space. It would alternatively be possible to select a 90 diopter objective which would flatten the image of objects to appear to have one-half the depth. Similarly, a 20 diopter lens would double the depth of the image. Thus, the lens 24 may be an exchangeable objective lens, although in the preferred embodiment, the lens 24 is a 45 diopter lens. When the lens 24 is exchanged, the change in the working distance does not affect the illumination, since the slit beam is parallel to the axis 20 in the object space. Of course, the lens 24 could be a variable power lens system.

As can be further appreciated, when the device 10 is used for imaging or for laser surgery, placing the border of the pupil within the field of view allows the image to be centered and referenced, while illumination using the single slit beam 21 is of good quality.

I claim:

1. A method of obtaining a scale-correct desired microscope image of a vitreous and a retina of an eye comprising the steps of:

providing a telescopic objective lens through which the vitreous and the retina of the eye can be imaged, the objective lens having an optical axis positioned to pass through a pupil of the eye;

projecting a slit beam in a fixed relation to the objective lens such that the slit beam passes through a focal point of the lens in an image space of the lens before passing through the lens, and the slit beam travels parallel to the optical axis of the lens in an object space of the lens between the lens and the eye where the slit beam enters the pupil; and adjusting a distance between the lens and the eye to obtain the desired microscope image.

2. The method as claimed in claim 1, wherein the objective lens is selected to have a power of approximately 45 diopters, whereby said image is spatially correct.

3. The method as claimed in claim 1, wherein the power of the objective lens is adjusted along with a working distance, said slit beam still remaining parallel to said optical axis in the object space of the lens.

4. An ophthalmic microscope comprising:

a telescopic objective lens having an optical axis;

a slit beam light source mounted in a fixed relation to the objective lens for producing a slit beam which passes through a focal point of the objective lens in an image space before passing through the objective lens, the slit beam traveling parallel to said optical axis in an object space of the objective lens; and field lens means for providing a spatially-correct microscope image through said objective lens of a vitreous and a retina of the eye.

5. The microscope as claimed in claim 4, further comprising a camera means.

6. The microscope as claimed in claim 4, further comprising laser means for laser surgery.

7. The microscope as claimed in claim 4, wherein said microscope is symmetrically telecentric.

8. The microscope as claimed in claim 4, wherein said objective lens has a power approximately three quarters of a power of a lens of an eye.

9. The microscope as claimed in claim 8, further comprising a camera means.

10. The microscope as claimed in claim 8, further comprising laser means for laser surgery.

11. The microscope as claimed in claim 8, wherein said microscope is symmetrically telecentric.

12. The microscope as claimed in claim 4, wherein said objective lens comprises variable power lens means.

\* \* \* \* \*

UNITED STATES PATENT AND TRADEMARK OFFICE
CERTIFICATE OF CORRECTION

PATENT NO. : 5,912,722
DATED : June 15, 1999
INVENTOR(S) : Kurt E. Schirmer

It is certified that error appears in the above-indentified patent and that said Letters Patent is hereby corrected as shown below:

The word "OPTHAMALIC" should read as -- OPHTHALMIC -- in the title of the patent.

Signed and Sealed this

Second Day of November, 1999

Attest:

Q. TODD DICKINSON

*Attesting Officer*   *Acting Commissioner of Patents and Trademarks*